US008658564B2

(12) United States Patent
Suty-Heinze et al.

(10) Patent No.: US 8,658,564 B2
(45) Date of Patent: Feb. 25, 2014

(54) FUNGICIDE ACTIVE INGREDIENT COMBINATIONS

(75) Inventors: Anne Suty-Heinze, Langenfeld (DE); Peter Dahmen, Neuss (DE)

(73) Assignee: Bayer Cropscience AG, Monheim (DE)

( * ) Notice: Subject to any disclaimer, the term of this patent is extended or adjusted under 35 U.S.C. 154(b) by 367 days.

(21) Appl. No.: 12/663,175

(22) PCT Filed: May 28, 2008

(86) PCT No.: PCT/EP2008/004216
§ 371 (c)(1),
(2), (4) Date: Dec. 4, 2009

(87) PCT Pub. No.: WO2008/148482
PCT Pub. Date: Dec. 11, 2008

(65) Prior Publication Data
US 2010/0298139 A1 Nov. 25, 2010

(30) Foreign Application Priority Data
Jun. 6, 2007 (EP) .................... 07011094

(51) Int. Cl.
*A01N 43/36* (2006.01)
*A01N 43/653* (2006.01)
*A01N 37/46* (2006.01)
*A01P 3/00* (2006.01)

(52) U.S. Cl.
USPC ........... 504/100; 514/383; 514/384; 514/406; 514/538

(58) Field of Classification Search
USPC ........... 514/383, 384, 406, 551, 538; 504/100
See application file for complete search history.

(56) References Cited

U.S. PATENT DOCUMENTS

| 3,912,752 | A | 10/1975 | Meiser et al. |
|---|---|---|---|
| 4,245,432 | A | 1/1981 | Dannelly |
| 4,272,417 | A | 6/1981 | Barke et al. |
| 4,294,850 | A | 10/1981 | Hubele |
| 4,425,357 | A | 1/1984 | Bosone et al. |
| 4,654,332 | A | 3/1987 | Parry et al. |
| 4,664,696 | A | 5/1987 | Schaub |
| 4,789,672 | A | 12/1988 | Holmwood et al. |
| 4,808,430 | A | 2/1989 | Kouno |
| 4,906,652 | A | 3/1990 | Karbach et al. |
| 5,081,141 | A | 1/1992 | Colle et al. |
| 5,306,712 | A | 4/1994 | Tobitsuka et al. |
| 5,723,491 | A | 3/1998 | Nuninger et al. |
| 5,789,430 | A | 8/1998 | Jautelat et al. |
| 5,876,739 | A | 3/1999 | Turnblad et al. |
| 2003/0176428 | A1 | 9/2003 | Schneidersmann et al. |
| 2005/0148639 | A1* | 7/2005 | Ammermann et al. ....... 514/355 |
| 2008/0269263 | A1 | 10/2008 | Dahmen et al. |
| 2009/0018015 | A1 | 1/2009 | Wachendorff-Neumann et al. |

FOREIGN PATENT DOCUMENTS

| CA | 1094079 | 1/1981 |
|---|---|---|
| CA | 1133492 | 10/1982 |
| CA | 2616719 | 3/2007 |
| EP | 0068813 | 1/1983 |
| EP | 0112284 | 6/1984 |
| EP | 0145294 | 6/1985 |
| EP | 0251775 | 1/1988 |
| EP | 0253714 | 1/1988 |
| EP | 0258161 | 3/1988 |
| EP | 0329397 | 8/1989 |
| EP | 0378953 | 7/1990 |
| GB | 1418430 | 12/1975 |
| GB | 1498199 | 1/1978 |
| GB | 2017496 | 10/1979 |
| GB | 2063260 | 6/1981 |
| WO | 98/26654 | 6/1998 |
| WO | 02/28186 | 4/2002 |
| WO | 02/080675 | 10/2002 |
| WO | WO 2005/041653 | * 5/2005 |
| WO | 2007/009775 | 1/2007 |

OTHER PUBLICATIONS

Hackh's Chemical Dictionary, 4th ed., McGraw-Hill Book Co., New York, 1977, p. 170.*
S.R. Colby, "Calculating Synergistic and Antagonistic Responses of Herbicide Combinations", Weeds, 1967, vol. 15, p. 20-22.
The Pesticide Manual, 13the Edition, 2003, p. 304, 468, 923-925.
International Search Report for PCT/EP2008/004216, mailed Sep. 24, 2008.

* cited by examiner

*Primary Examiner* — John Pak
(74) *Attorney, Agent, or Firm* — Miles & Stockbridge P.C.

(57) ABSTRACT

The present invention relates to novel active compound combinations comprising the known fungicidally active compounds N-[2-(1,3-dimethylbutyl)phenyl]-5-fluoro-1,3-dimethyl-1H-pyrazole-4-carboxamide, metalaxyl and triazole (3), which are highly suitable for controlling unwanted phytopathogenic fungi. Moreover, the invention relates to a method for the curative or preventive treatment of phytopathogenic fungi on plants or useful plants, in particular to the treatment of seed, for example seed of cereals, and not least to the treated seed itself.

15 Claims, No Drawings

FUNGICIDE ACTIVE INGREDIENT COMBINATIONS

CROSS REFERNCE TO RELATED APPLICATIONS

This application is a §371 National Stage Application of PCT/EP2008/004216 filed May 28, 2008, which claims priority to European Application 07011094.5 filed Jun. 6, 2007.

BACKGROUND OF THE INVENTION

1. Field of the Invention

The present invention relates to novel active compound combinations comprising the known fungicidally active compounds N-[2-(1,3-dimethylbutyl)phenyl]-5-fluoro-1,3-dimethyl-1H-pyrazole-4-carboxamide, acylalanines and triazoles, which are highly suitable for controlling unwanted phytopathogenic fungi. Moreover, the invention relates to a method for the curative or preventive treatment of phytopathogenic fungi on plants or useful plants, in particular to the treatment of seed, for example seed of cereals, and not least to the treated seed itself.

2. Description of Related Art

It is already known that N-[2-(1,3-dimethylbutyl)phenyl]-5-fluoro-1,3-dimethyl-1H-pyrazole-4-carboxamide, metalaxyl and triazole (3) have fungicidal properties [cf. The Pesticide Manual, 13th Edition (2003), pages 468f., 304f. and 923-925]. The activity of these compounds is good; however, in some cases it is unsatisfactory.

Since the ecological and economical demands made on modern fungicides are increasing constantly, for example with respect to activity spectrum, toxicity, selectivity, application rate, formation of residues and favourable manufacture, and there can furthermore be problems, for example, with resistance, there is a constant need to develop novel fungicides which, at least in some areas, help to overcome the disadvantages mentioned.

The present invention provides active compound combinations or compositions which achieve the object at least in some aspects.

SUMMARY OF THE INVENTION

Surprisingly, it has now been found that the active compound combinations or compositions according to the invention do not only exhibit an additive effect of the activity of the individual components, but a synergistic effect. Therefore, firstly, the customary application rate of the individual substances can be reduced. Secondly, the active compound combinations according to the invention offer a high degree of activity against phytopathogens even in cases where the individual compounds are employed in amounts where, for their part, they no longer show (sufficient) activity. In principle, this allows, firstly, the activity spectrum to be broadened and, secondly, better safety during handling.

In addition to the fungicidal synergistic activity, the active compound combinations according to the invention have further surprising properties which, in a wider sense, may also be called synergistic, such as, for example: broadening of the activity spectrum, for example to resistant pathogens of plant diseases; lower application rates of the active compounds; sufficient control of pests with the aid of the active compound combinations according to the invention even at application rates where the individual compounds show no or virtually no activity; advantageous behaviour during formulation or during use, for example during grinding, sieving, emulsifying, dissolving or application; improved storage stability and light stability; advantageous residue formation; improved toxicological or ecotoxicological behaviour; improved properties of the plant, for example better growth, increased harvest yields, a better developed root system, a larger leaf area, greener leaves, stronger shoots, less seed required, lower phytotoxicity, mobilization of the defence system of the plant, good compatibility with plants. Thus, the use of the active compound combinations or compositions according to the invention contributes considerably to keeping young plant stems healthy, which increases, for example, the winter survival of the cereal seed treated, and also safeguards quality and yield. Moreover, the active compound combinations according to the invention may contribute to enhanced systemic action. Even if the individual compounds of the combination have no sufficient systemic properties, the active compound combinations according to the invention may still have this property. In a similar manner, the active compound combinations according to the invention may result in higher persistency of the fungicidal action.

It has now been found that active compound combinations comprising
(1) N-[2-(1,3-dimethylbutyl)phenyl]-5-fluoro-1,3-dimethyl-1H-pyrazole-4-carboxamide or salts thereof, and
(2) at least one acylalanine of the general formula (I)

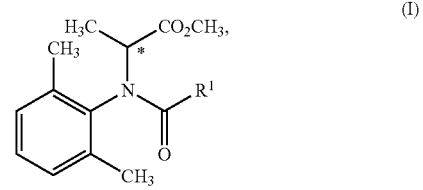

in which
* denotes a carbon atom in the R- or the S-configuration, preferably in the S-configuration,
$R^1$ represents benzyl, furyl or methoxymethyl, or its salt;
and
(3) at least one triazole of the general formula (II)

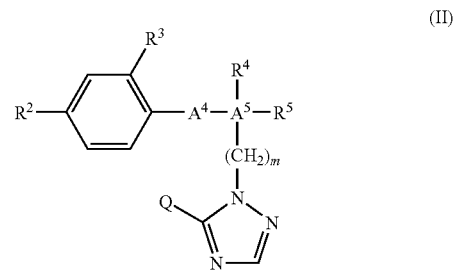

in which
Q represents hydrogen or SH,
m represents 0 or 1,
$R^2$ represents hydrogen, fluorine, chlorine, phenyl or 4-chlorophenoxy,
$R^3$ represents hydrogen or chlorine,
$A^4$ represents a direct bond, —$CH_2$—, —$(CH_2)_2$— or —O—,
$A^4$ furthermore represents *—$CH_2$—$CHR^{17}$— or *—CH=$CR^{17}$—, where the bond marked * is attached to the phenyl ring, in which case $R^{15}$ and $R^{17}$ together represent —$CH_2$—$CH_2$—CH[CH($CH_3$)$_2$]— or —$CH_2$—$CH_2$—C($CH_3$)$_2$—, $A^5$ represents C or Si (silicon), $R^4$ represents hydrogen, hydroxyl or cyano, $R^5$ represents 1-cyclopropylethyl, 1-chlorocyclopropyl, $C_1$-$C_4$-alkyl, $C_1$-$C_6$-hydroxyalkyl, $C_1$-$C_4$-alkylcarbonyl, $C_1$-$C_2$-haloalkoxy-$C_1$-$C_2$-alkyl, trimethylsilyl-$C_1$-$C_2$-alkyl, monofluorophenyl or phenyl, $R^4$ and $R^5$ furthermore together represent —O—$CH_2$—CH($R^6$)—O—, —O—$CH_2$—CH($R^6$)—$CH_2$— or —O—CH-(2-chlorophenyl)-, $R^6$ represents hydrogen, $C_1$-$C_4$-alkyl or bromine, or its salt, have very good fungicidal properties.

DETAILED DESCRIPTION OF A PREFERRED EMBODIMENT

If the active compounds in the active compound combinations according to the invention are present in certain weight ratios, the synergistic effect is particularly pronounced. However, the weight ratios of the active compounds in the active compound combinations can be varied within a relatively wide range.

In general, 0.005-500, preferably 0.01-100, particularly preferably 0.05-50, very particularly preferably 0.1-10, parts by weight of acylalanine (2) and 0.005-500, preferably 0.01-100, particularly preferably 0.05-50, very particularly preferably 0.1-10, parts by weight of N-[2-(1,3-dimethylbutyl)phenyl]-5-fluoro-1,3-dimethyl-1H-pyrazole-4-carboxamide are present per part by weight of triazole (3).

The active compounds triazole (3), acylalanine (2) and N-[2-(1,3-dimethylbutyl)phenyl]-5-fluoro-1,3-dimethyl-1H-pyrazole-4-carboxamide may optionally be present in the form of their salts.

The acylalanines (2) of the formula (I) are preferably selected from the group consisting of:

(2-1) benalaxyl (known from DE-A 29 03 612) of the formula

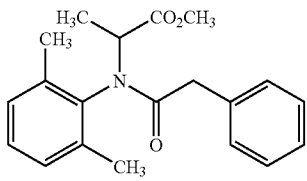 [SMILES: COC(=O)C(C)N(C(=O)Cc1ccccc1)c1c(C)cccc1C]

(2-2) furalaxyl (known from DE-A 25 13 732) of the formula

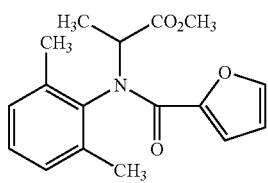 [SMILES: COC(=O)C(C)N(C(=O)c1ccco1)c1c(C)cccc1C]

(2-3) metalaxyl (known from DE-A 25 15 091) of the formula

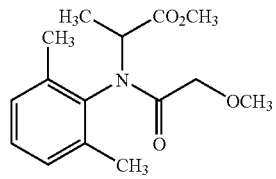 [SMILES: COCC(=O)N(c1c(C)cccc1C)C(C)C(=O)OC]

(2-4) metalaxyl-M (known from WO 96/01559) of the formula

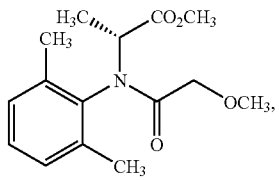

with metalaxyl and metalaxyl-M being particularly preferred.

The triazoles (3) of the formula (II) are preferably selected from the group consisting of:

(3-1) azaconazole (known from DE-A 25 51 560) of the formula

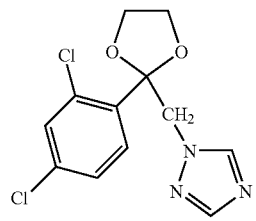 [SMILES: Clc1ccc(C2(Cn3cncn3)OCCO2)c(Cl)c1]

(3-2) etaconazole (known from DE-A 25 51 560) of the formula

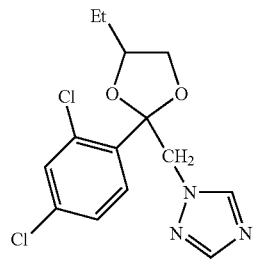 [SMILES: CCC1COC(Cn2cncn2)(c2ccc(Cl)cc2Cl)O1]

(3-3) propiconazole (known from DE-A 25 51 560) of the formula

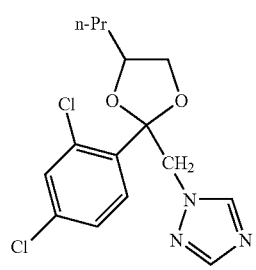

(3-4) difenoconazole (known from EP-A 0 112 284) of the formula

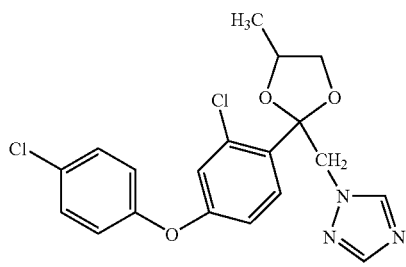 [SMILES: CC1COC(Cn2cncn2)(c2ccc(Oc3ccc(Cl)cc3)cc2Cl)O1]

(3-5) bromuconazole (known from EP-A 0 258 161) of the formula

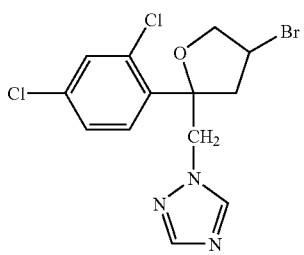 [SMILES: Clc1ccc(C2(Cn3cncn3)CC(Br)CO2)c(Cl)c1]

(3-6) cyproconazole (known from DE-A 34 06 993) of the formula

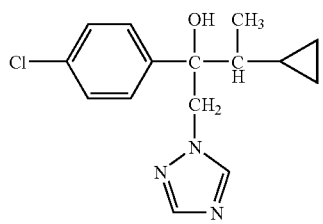 [SMILES: CC(C1CC1)C(O)(Cn1cncn1)c1ccc(Cl)cc1]

(3-7) hexaconazole (known from DE-A 30 42 303) of the formula

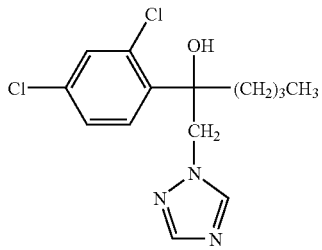

(3-8) penconazole (known from DE-A 27 35 872) of the formula

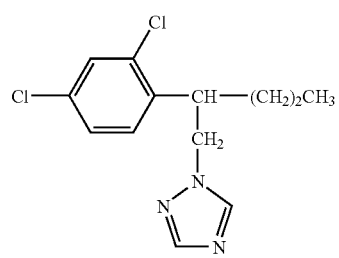

(3-9) myclobutanil (known from EP-A 0 145 294) of the formula

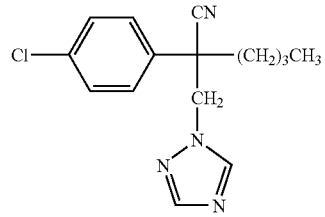

(3-10) tetraconazole (known from EP-A 0 234 242) of the formula

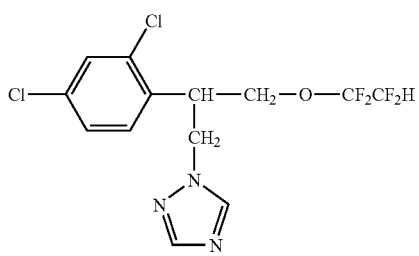

(3-11) flutriafol (known from EP-A 0 015 756) of the formula

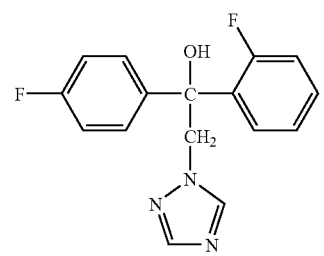 [SMILES: OC(Cn1cncn1)(c1ccc(F)cc1)c1ccccc1F]

(3-12) epoxiconazole (known from EP-A 0 196 038) of the formula

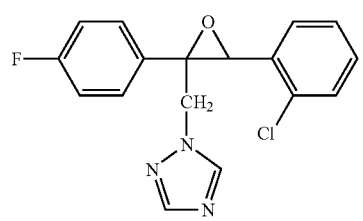 [SMILES: Fc1ccc(C2(Cn3cncn3)OC2c2ccccc2Cl)cc1]

(3-13) flusilazole (known from EP-A 0 068 813) of the formula

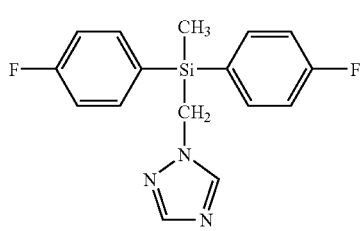 [SMILES: C[Si](Cn1cncn1)(c1ccc(F)cc1)c1ccc(F)cc1]

(3-14) simeconazole (known from EP-A 0 537 957) of the formula

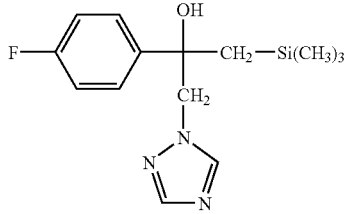

(3-15) prothioconazole (known from WO 96/16048) of the formula

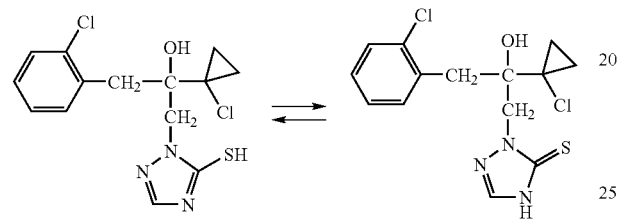

(3-16) fenbuconazole (known from DE-A 37 21 786) of the formula

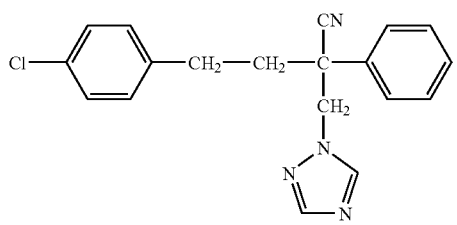 [SMILES: N#CC(CCc1ccc(Cl)cc1)(Cn1cncn1)c1ccccc1]

(3-17) tebuconazole (known from EP-A 0 040 345) of the formula

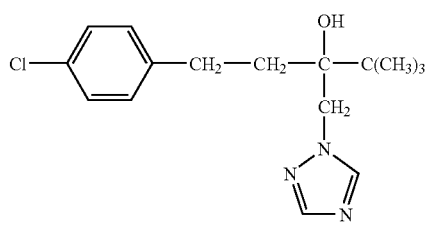 [SMILES: CC(C)(C)C(O)(CCc1ccc(Cl)cc1)Cn1cncn1]

(3-18) ipconazole (known from EP-A 0 329 397) of the formula

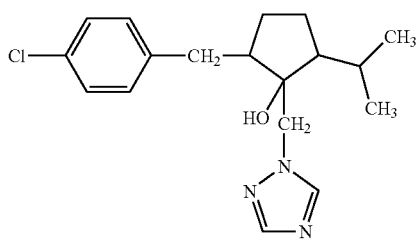 [SMILES: CC(C)C1CCC(Cc2ccc(Cl)cc2)C1(O)Cn1cncn1]

(3-19) metconazole (known from EP-A 0 329 397) of the formula

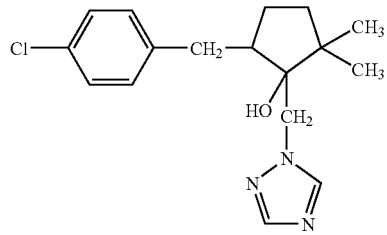 [SMILES: CC1(C)CCC(Cc2ccc(Cl)cc2)C1(O)Cn1cncn1]

(3-20) triticonazole (known from EP-A 0 378 953) of the formula

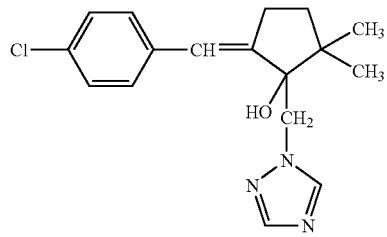 [SMILES: CC1(C)CCC(=Cc2ccc(Cl)cc2)C1(O)Cn1cncn1]

(3-21) bitertanol (known from DE-A 23 24 010) of the formula

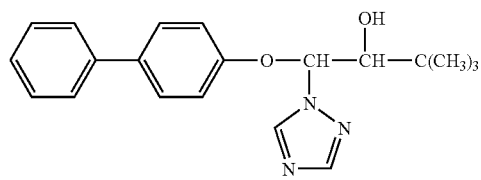 [SMILES: CC(C)(C)C(O)C(Oc1ccc(-c2ccccc2)cc1)n1cncn1]

(3-22) triadimenol (known from DE-A 23 24 010) of the formula

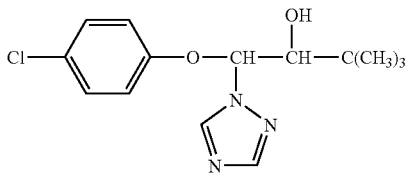 [SMILES: CC(C)(C)C(O)C(Oc1ccc(Cl)cc1)n1cncn1]

(3-23) triadimefon (known from DE-A 22 01 063) of the formula

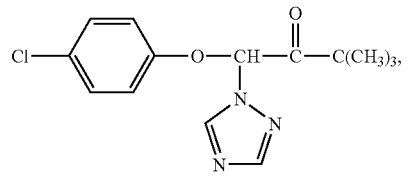

(3-24) diniconazole,
(3-25) diniconazole-M,
(3-26) fluquinconazole,
(3-27) imazalil,
(3-28) imazalil sulphate and
(3-29) prochloraz and salts and/or mixtures of these,
with tebuconazole (107534-96-3), (chemical name: (RS)-1-p-chlorophenyl-4,4-dimethyl-3-(1H-1,2,4-triazol-1-ylmethyl)-pentan-3-ol) or its salts being particularly preferred.

Particularly preferably, N-[2-(1,3-dimethylbutyl)phenyl]-5-fluoro-1,3-dimethyl-1H-pyrazole-4-carboxamide is combined with the following mixing partners (2) and (3):

(2-1) benalaxyl and at least one azole selected from the group consisting of (3-1) azaconazole, (3-2) etaconazole, (3-3) propiconazole, (3-4) difenoconazole, (3-5) bromuconazole, (3-6) cyproconazole, (3-7) hexaconazole, (3-8) penconazole, (3-9) myclobutanil, (3-10) tetraconazole, (3-11) flutriafol, (3-12) epoxiconazole, (3-13) flusilazole, (3-14) simeconazole, (3-15) prothioconazole, (3-16)fenbuconazole, (3-17) tebuconazole, (3-18) ipconazole, (3-19) metconazole, (3-20) triticonazole, (3-21) bitertanol, (3-22) triadimenol, (3-23) triadimefon, (3-24) diniconazole, (3-25) diniconazole-M, (3-26) fluquinconazole, (3-27) imazalil, (3-28) imazalil sulphate and (3-29) prochloraz and salts and/or mixtures of these.

(2-2) furalaxyl and at least one azole selected from the group consisting of (3-1) azaconazole, (3-2) etaconazole, (3-3) propiconazole, (3-4) difenoconazole, (3-5) bromuconazole, (3-6) cyproconazole, (3-7) hexaconazole, (3-8) penconazole, (3-9) myclobutanil, (3-10) tetraconazole, (3-11) flutriafol, (3-12) epoxiconazole, (3-13) flusilazole, (3-14) simeconazole, (3-15) prothioconazole, (3-16) fenbuconazole, (3-17) tebuconazole, (3-18) ipconazole, (3-19) metconazole, (3-20) triticonazole, (3-21) bitertanol, (3-22) triadimenol, (3-23) triadimefon, (3-24) diniconazole, (3-25) diniconazole-M, (3-26) fluquinconazole, (3-27) imazalil, (3-28) imazalil sulphate and (3-29) prochloraz and salts and/or mixtures of these.

(2-3) metalaxyl and at least one azole selected from the group consisting of (3-1) azaconazole, (3-2) etaconazole, (3-3) propiconazole, (3-4) difenoconazole, (3-5) bromuconazole, (3-6) cyproconazole, (3-7) hexaconazole, (3-8) penconazole, (3-9) myclobutanil, (3-10) tetraconazole, (3-11) flutriafol, (3-12) epoxiconazole, (3-13) flusilazole, (3-14) simeconazole, (3-15) prothioconazole, (3-16) fenbuconazole, (3-17) tebuconazole, (3-18) ipconazole, (3-19) metconazole, (3-20) triticonazole, (3-21) bitertanol, (3-22) triadimenol, (3-23) triadimefon, (3-24) diniconazole, (3-25) diniconazole-M, (3-26) fluquinconazole, (3-27) imazalil, (3-28) imazalil sulphate and (3-29) prochloraz and salts and/or mixtures of these.

(2-4) metalaxyl-M and at least one azole selected from the group consisting of (3-1) azaconazole, (3-2) etaconazole, (3-3) propiconazole, (3-4) difenoconazole, (3-5) bromuconazole, (3-6) cyproconazole, (3-7) hexaconazole, (3-8) penconazole, (3-9) myclobutanil, (3-10) tetraconazole, (3-11) flutriafol, (3-12) epoxiconazole, (3-13) flusilazole, (3-14) simeconazole, (3-15) prothioconazole, (3-16) fenbuconazole, (3-17) tebuconazole, (3-18) ipconazole, (3-19) metconazole, (3-20) triticonazole, (3-21) bitertanol, (3-22) triadimenol, (3-23) triadimefon, (3-24) diniconazole, (3-25) diniconazole-M, (3-26) fluquinconazole, (3-27) imazalil, (3-28) imazalil sulphate and (3-29) prochloraz and salts and/or mixtures of these.

According to the invention, the term "active compound combination" means various possible combinations of the three active compounds mentioned above, such as, for example, readymixes, tank mixes (which is to be understood as meaning spray mixtures prepared prior to application from the formulations of the individual active compounds by mixing and diluting) or combinations thereof (for example, a binary readymix of two of the active compounds mentioned above is converted with a formulation of the third individual substance into a tank mix). According to the invention, the individual active compounds may also be used successively, i.e. one after the other, within a reasonable interval of a few hours or days, and, in the treatment of seed, also, for example, by applying a plurality of layers comprising different active compounds. Preferably, it is immaterial in which order the individual active compounds may be employed.

The present invention furthermore relates to compositions comprising the active compound combinations according to the invention. Preferably, the compositions are fungicidal compositions comprising agriculturally suitable carriers or extenders.

According to the invention, carrier is to be understood as meaning a natural or synthetic, organic or inorganic substance which is mixed or combined with the active compounds for better applicability, in particular for application to plants or plant parts or seeds. The carrier, which may be solid or liquid, is generally inert and should be suitable for use in agriculture.

Suitable solid carriers are: for example ammonium salts and natural ground minerals, such as kaolins, clays, talc, chalk, quartz, attapulgite, montmorillonite or diatomaceous earth, and ground synthetic minerals, such as finely divided silica, alumina and natural or synthetic silicates, resins, waxes, solid fertilizers, water, alcohols, especially butanol, organic solvents, mineral oils and vegetable oils, and also derivatives thereof. It is also possible to use mixtures of such carriers. Solid carriers suitable for granules are: for example crushed and fractionated natural minerals, such as calcite, marble, pumice, sepiolite, dolomite, and also synthetic granules of inorganic and organic meals and also granules of organic material, such as sawdust, coconut shells, maize cobs and tobacco stalks. Suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, and also protein hydrolysates. Suitable dispersants are: for example lignosulphite waste liquors and methylcellulose.

Suitable liquefied gaseous extenders or carriers are liquids which are gaseous at ambient tempertature and under atmospheric pressure, for example aerosol propellants, such as butane, propane, nitrogen and carbon dioxide.

Tackifiers, such as carboxymethylcellulose and natural and synthetic polymers in the form of powders, granules and latices, such as gum arabic, polyvinyl alcohol, polyvinyl acetate, or else natural phospholipids, such as cephalins and lecithins and synthetic phospholipids can be used in the formulations. Other possible additives are mineral and vegetable oils.

If the extender used is water, it is also possible for example, to use organic solvents as auxiliary solvents. Suitable liquid solvents are essentially: aromatic compounds, such as xylene, toluene or alkylnaphthalenes, chlorinated aromatic compounds or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol, and also ethers and esters thereof, ketones, such as acetone, methyl ethyl ketone, methyl isobutyl ketone or cyclohexanone, strongly polar solvents, such as dimethylformamide and dimethyl sulphoxide, and also water.

The compositions according to the invention may comprise additional further components, such as, for example, surfactants. Suitable surfactants are emulsifiers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates. The presence of a surfactant is required if one of the active compounds and/or one of the inert carriers is insoluble in water and when the application takes place in water. The proportion of surfactants is between 5 and 40 percent by weight of the composition according to the invention.

It is possible to use colorants such as inorganic pigments, for example iron oxide, titanium oxide, Prussian blue, and organic dyes, such as alizarin dyes, azo dyes and metal phthalocyanine dyes, and trace nutrients, such as salts of iron, manganese, boron, copper, cobalt, molybdenum and zinc.

If appropriate, other additional components may also be present, for example protective colloids, binders, adhesives, thickeners, thixotropic substances, penetrants, stabilizers, sequestring agents, complex formers. In general, the active compounds can be combined with any solid or liquid additive customarily used for formulation purposes.

In general, the compositions according to the invention comprise between 0.05 and 99 percent by weight of the active compound combination according to the invention, preferably between 5 and 60 percent by weight, particularly preferably between 10 and 50 percent by weight, very particularly preferably 20 percent by weight.

The active compound combinations or compositions according to the invention can be used as such or, depending on their respective physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide-coated seed, suspension concentrates, suspoemulsion concentrates, soluble concentrates, suspensions, wettable powders, soluble powders, dusts and granules, water-soluble granules or tablets, water-soluble powders for the treatment of seed, wettable powders, natural products and synthetic substances impregnated with active compound, and also microencapsulations in polymeric substances and in coating materials for seed, and also ULV cold-fogging and warm-fogging formulations.

The formulations mentioned can be prepared in a manner known per se, for example by mixing the active compounds or the active compound combinations with at least one solvent or diluent, emulsifier, dispersant and/or binder or fixing agent, water repellant, appropriate siccatives and UV stabilizers and, if appropriate, dyes and pigments, and also further processing auxiliaries.

The treatment according to the invention of the plants and plant parts with the active compound combinations or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more coats, etc.

The compositions according to the invention do not only comprise ready-to-use compositions which can be applied with suitable apparatus to the plant or the seed, but also commercial concentrates which have to be diluted with water prior to use.

The active compound combinations according to the invention can be present in commercial formulations and in the use forms prepared from these formulations as a mixture with other active compounds, such as insecticides, attractants, sterilants, bactericides, acaricides, nematicides, fungicides, growth regulators or herbicides.

The active compound combinations or compositions according to the invention have strong microbicidal activity and can be used for controlling unwanted microorganisms, such as fungi and bacteria, in crop protection and in the protection of materials.

In crop protection, fungicides can be used for controlling Plasmodiophoromycetes, Oomycetes, Chytridiomycetes, Zygomycetes, Ascomycetes, Basidiomycetes and Deuteromycetes.

In crop protection, bactericides can be used for controlling Pseudomonadaceae, Rhizobiaceae, Enterobacteriaceae, Corynebacteriaceae and Streptomycetaceae.

The fungicidal compositions according to the invention can be used for the curative or protective control of phytopathogenic fungi. Accordingly, the invention also relates to curative and protective methods for controlling phytopathogenic fungi using the active compound combinations or compositions according to the invention, which are applied to the seed, the plant or plant parts, the fruit or the soil in which the plants grow.

According to the invention, it is possible to treat all plants and parts of plants. Plants are to be understood here as meaning all plants and plant populations, such as wanted and unwanted wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by varietal property rights. Parts of plants are to be understood as meaning all above-ground and below-ground parts and organs of the plants, such as shoot, leaf, flower and root, examples which may be mentioned being leaves, needles, stems, trunks, flowers, fruit bodies, fruits and seeds and also roots, tubers and rhizomes. Plant parts also include harvested material and vegetative and generative propagation material, for example seedlings, tubers, rhizomes, cuttings and seeds.

The following plants may be mentioned as plants which can be treated according to the invention: cotton, flax, grapevines, fruit, vegetable, such as *Rosaceae* sp. (for example pomaceous fruit, such as apples and pears, but also stone fruit, such as apricots, cherries, almonds and peaches and soft fruit such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit), *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumbers), *Alliaceae* sp. (for example leek, onions), *Papilionaceae* sp. (for example peas); major crop plants, such *Gramineae* sp. (for example maize, lawn, cereals such as wheat, rye, rice, barley, oats, millet and triticale), *Asteraceae* sp. (for example sunflowers), *Brassicaceae* sp. (for example white cabbage, red cabbage, broccoli, cauliflowers, brussel sprouts, pak choi, kohlrabi, garden radish, and also oilseed rape, canola, mustard, horseradish and cress), *Fabacae* sp. (for example beans, peas, lentils, peanuts), *Papilionaceae* sp. (for example soya beans), *Solanaceae* sp. (for example potatoes), *Chenopodiaceae* sp. (for example sugarbeet, fodderbeet, swiss chard, beetroot); crop plants and ornamental plants in garden and forest; and also in each case genetically modified varieties of these plants.

The method according to the invention for controlling phytopathogenic fungi can also be employed for treating genetically modified organisms, for example plants or seeds. Genetically modified plants are plants whose genome has, stably integrated, a certain heterologous gene coding for a certain protein. Here, "heterologous gene" is meant to be understood as a gene which confers novel agronomical properties on the transformed plant, or a gene which improves the agronomical quality of the modified plant.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The terms "parts", "parts of plants" and "plant parts" have been explained above. Particularly preferably, plants of the plant cultivars which are in each case commercially available or in use are treated according to the invention.

Depending on the plant species or plant cultivars, their location and growth conditions (soil, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars (obtained by genetic engineering) which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the imprtant crop plants, such as cereals (wheat, rice), vegetables (tomato), maize, soya beans, potatoes, cotton, oilseed rape, canola, and also fruit plants (with the fruits apples, pears, citrus fruits and grapes), and particular emphasis is given to rice, maize, soya beans, potatoes, cotton, tomato, canola and oilseed rape.

The mixture of N-[2-(1,3-dimethylbutyl)phenyl]-5-fluoro-1,3-dimethyl-1H-pyrazole-4-carboxamide, tebuconazole and metalaxyl is particularly preferred for the following crops: cereals, maize, soya beans, oilseed rape, canola, vegetables (in particular tomatoes), potatoes, cotton, sunflowers, leguminous plants (peas, beans, lentils . . . ).

Furthermore, the mixture N-[2-(1,3-dimethylbutyl)phenyl]-5-fluoro-1,3-dimethyl-1H-pyrazole-4-carboxamide, prothioconazole and metalaxyl is particularly preferred for the following crops: cereals, maize, soya beans, oilseed rape, canola, vegetables (in particular tomatoes), potatoes, cotton, sunflowers, leguminous plants (peas, beans, lentils, etc.).

"Traits" that are emphasized are in particular increased defense of the plants against insects by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasized are the increased tolerance of the plants to certain herbicidally active compounds, for example imidazolinones, sulphonylureas, glyphosate or phosphinothricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potatoes). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieites sold under the name Clearfield® (for example maize). Of course, these statements also apply to plant cultivars having these genetic traits or genetic traits still to be developed, which plant cultivars will be developed and/or marketed in the future.

Moreover, the active compound combinations according to the invention can be used in the protection of materials for protecting industrial materials against unwanted fungi. Industrial materials are, for example, paper, carpets, buildings, cooling and heating systems, wall coverings, insulation and air conditioning units. The active compound combinations according to the invention may prevent disadvantageous effects, such as rotting, decay, discolouration, decolouration or formation of mould.

The method according to the invention for controlling unwanted fungi can also be employed for protecting storage goods. Here, storage goods are to be understood as meaning natural substances of vegetable or animal origin or processed products thereof of natural origin, for which long-term protection is desired. Storage goods of vegetable origin, such as, for example, plants or plant parts, such stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The active compound combinations according to the invention can prevent disadvantageous effects, such as rotting, decay, discolouration, decolouration or the formation of mould.

Some pathogens of fungal or bacterial diseases which can be treated according to the invention may be mentioned by way of example, but not by way of limitation:

Diseases caused by powdery mildew pathogens, such as, for example,

Blumeria species, such as, for example, *Blumeria graminis*;
Podosphaera species, such as, for example, *Podosphaera leucotricha*;
Sphaerotheca species, such as, for example, *Sphaerotheca fuliginea*;
Uncinula species, such as, for example, *Uncinula necator*;
Diseases caused by rust disease pathogens, such as, for example,
Gymnosporangium species, such as, for example, *Gymnosporangium sabinae*
Hemileia species, such as, for example, *Hemileia vastatrix*;
Phakopsora species, such as, for example, *Phakopsora pachyrhizi* and *Phakopsora meibomiae*;
Puccinia species, such as, for example, *Puccinia recondita* or *Puccinia triticina*;
Uromyces species, such as, for example, *Uromyces appendiculatus*;
Diseases caused by pathogens from the group of the Oomycetes, such as, for example,
Bremia species, such as, for example, *Bremia lactucae*;
Peronospora species, such as, for example, *Peronospora pisi* or *P. brassicae*;
Phytophthora species, such as, for example *Phytophthora infestans*;
Plasmopara species, such as, for example, *Plasmopara viticola*;
Pseudoperonospora species, such as, for example, *Pseudoperonospora humuli* or *Pseudoperonospora cubensis*;
Pythium species, such as, for example, *Pythium ultimum*;
Leaf blotch diseases and leaf wilt diseases caused, for example, by
Alternaria species, such as, for example, *Alternaria solani*;
Cercospora species, such as, for example, *Cercospora beticola*;
Cladiosporium species, such as, for example, *Cladiosporium cucumerinum*;
Cochliobolus species, such as, for example, *Cochliobolus sativus*
(conidia form: *Drechslera*, Syn: *Helminthosporium*);
Colletotrichum species, such as, for example, *Colletotrichum lindemuthanium*;
Cycloconium species, such as, for example, *Cycloconium oleaginum*;
Diaporthe species, such as, for example, *Diaporthe citri*;
Elsinoe species, such as, for example, *Elsinoe fawcettii*;
Gloeosporium species, such as, for example, *Gloeosporium laeticolor*;
Glomerella species, such as, for example, *Glomerella cingulata*;
Guignardia species, such as, for example, *Guignardia bidwelli*;
Leptosphaeria species, such as, for example, *Leptosphaeria maculans*;
Magnaporthe species, such as, for example, *Magnaporthe grisea*;
Mycosphaerella species, such as, for example, *Mycosphaerella graminicola* and *M. fijiensis*;
Phaeosphaeria species, such as, for example, *Phaeosphaeria nodorum*;
Pyrenophora species, such as, for example, *Pyrenophora teres*;
Ramularia species, such as, for example, *Ramularia collocygni*;
Rhynchosporium species, such as, for example, *Rhynchosporium secalis*;
Septoria species, such as, for example, *Septoria apii*;
Typhula species, such as, for example, *Typhula incarnata*;
Venturia species, such as, for example, *Venturia inaequalis*;
Root and stem diseases caused, for example, by
Corticium species, such as, for example, *Corticium graminearum*;
Fusarium species, such as, for example, *Fusarium oxysporum*;
Gaeumannomyces species, such as, for example, *Gaeumannomyces graminis*;
Rhizoctonia species, such as, for example *Rhizoctonia solani*;
Tapesia species, such as, for example, *Tapesia acuformis*;
Thielaviopsis species, such as, for example, *Thielaviopsis basicola*;
Ear and panicle diseases (including maize cobs) caused, for example, by
Alternaria species, such as, for example, *Alternaria* spp.;
Aspergillus species, such as, for example, *Aspergillus flavus*;
Cladosporium species, such as, for example, *Cladosporium cladosporioides*;
Claviceps species, such as, for example, *Claviceps purpurea*;
Fusarium species, such as, for example, *Fusarium culmorum*;
Gibberella species, such as, for example, *Gibberella zeae*;
Monographella species, such as, for example, *Monographella nivalis*;
Diseases caused by smut fungi, such as, for example,
Sphacelotheca species, such as, for example, *Sphacelotheca reiliana*;
Tilletia species, such as, for example, *Tilletia caries*;
Urocystis species, such as, for example, *Urocystis occulta*;
Ustilago species, such as, for example, *Ustilago nuda*;
Fruit rot caused, for example, by
Aspergillus species, such as, for example, *Aspergillus flavus*;
Botrytis species, such as, for example, *Botrytis cinerea*;
Penicillium species, such as, for example, *Penicillium expansum* and *P. purpurogenum*;
Sclerotinia species, such as, for example, *Sclerotinia sclerotiorum*;
Verticilium species, such as, for example, *Verticilium alboatrum*;
Seed- and soil-borne rot and wilt diseases, and also diseases of seedlings, caused, for example, by
Alternaria species, such as, for example, *Alternaria brassicicola*
Aphanomyces species, such as, for example, *Aphanomyces euteiches*
Ascochyta species, such as, for example, *Ascochyta lentis*
Aspergillus species, such as, for example, *Aspergillus flavus*
Cladosporium species, such as, for example, *Cladosporium herbarum*
Cochliobolus species, such as, for example, *Cochliobolus sativus*
(conidia form: *Drechslera, Bipolaris* Syn: *Helminthosporium*);
Colletotrichum species, such as, for example, *Colletotrichum coccodes*;

*Fusarium* species, such as, for example, *Fusarium culmorum;*

*Gibberella* species, such as, for example, *Gibberella zeae;*

*Macrophomina* species, such as, for example, *Macrophomina phaseolina*

*Monographella* species, such as, for example, *Monographella nivalis;*

*Penicillium* species, such as, for example, *Penicillium expansum*

*Phaeosphaeria* species, such as, for example, *Phaeosphaeria nodorum;*

*Phoma* species, such as, for example, *Phoma lingam*

*Phomopsis* species, such as, for example, *Phomopsis sojae;*

*Phytophthora* species, such as, for example, *Phytophthora cactorum;*

*Pyrenophora* species, such as, for example, *Pyrenophora graminea*

*Pyricularia* species, such as, for example, *Pyricularia oryzae;*

*Pythium* species, such as, for example, *Pythium ultimum;*

*Rhizoctonia* species, such as, for example, *Rhizoctonia solani;*

*Rhizopus* species, such as, for example, *Rhizopus oryzae*

*Sclerotium* species, such as, for example, *Sclerotium rolfsii;*

*Typhula* species, such as, for example, *Typhula incarnata;*

*Verticillium* species, such as, for example, *Verticillium dahliae*

Cancerous diseases, galls and witches' broom caused, for example, by

*Nectria* species, such as, for example, *Nectria galligena;*

Wilt diseases caused, for example, by

*Monilinia* species, such as, for example, *Monilinia laxa;*

Deformations of leaves, flowers and fruits caused, for example, by

*Taphrina* species, such as, for example, *Taphrina deformans;*

Degenerative diseases of woody plants caused, for example, by

*Esca* species, such as, for example, *Phaemoniella clamydospora* and *Phaeoacremonium aleophilum* and *Fomitiporia mediterranea;*

Diseases of flowers and seeds caused, for example, by

*Botrytis* species, such as, for example, *Botrytis cinerea;*

Diseases of plant tubers caused, for example, by

*Rhizoctonia* species, such as, for example, *Rhizoctonia solani;*

*Helminthosporium* species, such as, for example, *Helminthosporium solani;*

Diseases caused by bacteriopathogens, such as, for example,

*Xanthomonas* species, such as, for example, *Xanthomonas campestris* pv. *oryzae;*

*Pseudomonas* species, such as, for example, *Pseudomonas syringae* pv. *lachrymans;*

*Erwinia* species, such as, for example, *Erwinia amylovora.*

Preference is given to controlling the following diseases of soya beans:

fungal diseases on leaves, stems, pods and seeds caused, for example, by alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi Phakopsora meibomiae*), scab (*Sphaceloma glycines*), stemphylium leaf blight (*Stemphylium botryosum*), target spot (*Corynespora cassiicola*)

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmopspora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia Southern blight (*Sclerotinia rolfsii*), thielaviopsis root rot (*Thielaviopsis basicola*).

The application rate of the active compound combinations according to the invention is when treating leaves: from 0.1 to 10 000 g/ha, preferably from 10 to 1 000 g/ha, particularly preferably from 50 to 300 g/ha (when the application is carried out by watering or dripping, it may even be possible to reduce the application rate, in particular when inert substrates such as rock wool or perlite are used);

when treating seed: from 0.01 to 200 g per 100 kg of seed, preferably from 0.1 to 150 g per 100 kg of seed, particularly preferably from 5 to 25 g per 100 kg of seed;

when treating the soil: from 0.1 to 10 000 g/ha, preferably from 1 to 5 000 g/ha.

These application rates are mentioned only by way of example and not by way of limitation in the sense of the invention.

The active compound combinations or compositions according to the invention can thus be employed for protecting plants for a certain period of time after treatment against attack by the pathogens mentioned.

The period for which protection is provided extends generally for 1 to 28 days, preferably 1 to 14 days, after the treatment of the plants with the active compounds, or for up to 200 days after seed treatment.

The active compound combinations or compositions according to the invention can also be used for preparing a medicament for the curative or protective treatment of humans or animals against fungal diseases, such as mycoses, dermatoses, *Trichophyton* diseases and candidases or diseases caused by *Aspergillus* spp., such as *A. fumigatus.*

In addition, by the treatment according to the invention it is possible to reduce the mycotoxin content in the harvested material and the foodstuff and feedstuff prepared therefrom. Particular, but not exclusive, mention may be made here of the following mycotoxins: deoxynivalenol (DON), nivalenol, 15-Ac-DON, 3-Ac-DON, T2- and HT2-toxin, fumonisine, zearalenon, moniliformin, fusarin, diaceotoxyscirpenol (DAS), beauvericin, enniatin, fusaroproliferin, fusarenol, ochratoxins, patulin, ergot alkaloids and aflatoxins produced, for example, by the following fungi: *Fusarium* spec., such as *Fusarium acuminatum, F. avenaceumi F. crookwellense, F. culmorum, F. graminearum* (*Gibberella zeae*), *F. equiseti, F.*

*fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides,* inter alia, and also by *Aspergillus* spec., *Penicillium* spec., *Claviceps purpurea, Stachybotrys* spec. inter alia.

The invention furthermore comprises a method for treating seed where the individual active compounds are applied simultaneously to the seed. Moreover, the invention comprises a method for treating seed where the individual active compounds are applied successively to the seed. Moreover, the invention comprises a method for treating seed where an individual active compound is applied first, followed by a binary mixture of the two other active compounds. Alternatively, it is also possible to apply to the seed first a binary mixture, followed by the remaining individual active compound. If active compounds and/or individual active compounds and binary mixtures are applied separately, this is preferably carried out as different layers. These layers may additionally be separated by layers without active compound.

The invention furthermore relates to seed treated according to one of the methods described in the preceding paragraph.

The active compound combinations or compositions according to the invention are especially suitable for treating seed. A large part of the damage to crop plants caused by harmful organisms is triggered by an infection of the seed during storage or after sowing both during and after germination of the plant. This phase is particularly critical since the roots and shoots of the growing plant are particularly sensitive, and even small damage may result in the death of the plant. Accordingly, there is great interest in protecting the seed and the germinating plant by using appropriate compositions.

The control of phytopathogenic fungi by treating the seed of plants has been known for a long time and is subject of continuous improvements. However, the treatment of seed entails a series of problems which cannot always be solved in a satisfactory manner. Thus, it is desirable to develop methods for protecting the seed and the germinating plant which dispense with the additional application of crop protection agents after sowing or after the emergence of the plants or where additional application which at least considerably reduce. It is furthermore desirable to optimize the amount of active compound employed in such a way as to provide maximum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection agents being employed.

Accordingly, the present invention also relates in particular to a method for protecting seed and germinating plants against attack by phytopathogenic fungi by treating the seed with a composition according to the invention. The invention also relates to the use of the compositions according to the invention for treating seed for protecting the seed and the germinating plant against phytopathogenic fungi. Furthermore, the invention relates to seed treated with a composition according to the invention for protection against phytopathogenic fungi.

The control of phytopathogenic fungi which damage plants post-emergence is carried out primarily by treating the soil and the above-ground parts of plants with crop protection compositions. Owing to the concerns regarding a possible impact of the crop protection composition on the environment and the health of humans and animals, there are efforts to reduce the amount of active compounds applied.

One of the advantages of the present invention is that, because of the particular systemic properties of the compositions according to the invention, treatment of the seed with these compositions not only protects the seed itself, but also the resulting plants after emergence, from phytopathogenic fungi. In this manner, the immediate treatment of the crop at the time of sowing or shortly thereafter can be dispensed with.

It is also considered to be advantageous that the compositions according to the invention can be used in particular also for transgenic seed where the plant growing from this seed is capable of expressing a protein which acts against pests. By treating such seed with the active compound combinations or compositions according to the invention, even by the expression of the, for example, insecticidal protein, certain pests may be controlled. Surprisingly, a further synergistic effect may be observed here, which additionally increases the effectiveness of the protection against attack by pests.

The compositions according to the invention are suitable for protecting seed of any plant variety employed in agriculture, in the greenhouse, in forests or in horticulture or viticulture. In particular, this takes the form of seed of maize, peanuts, oilseed rape, canola, poppies, olives, coconuts, cocao, soya bean, beets (for example sugarbeets and fodder beets), rice, millet, wheat, barley, rye, oats, cotton, potatoes, sunflowers, sugarcane, tobacco, beans, coffee, vegetables (such as tomatoes, cucumbers, onions and lettuce), leguminous plants (beans, peas, lentils), lawn and ornamental plants.

As already described, the treatment of transgenic seed with the active compound combinations or compositions according to the invention is of particular importance. This refers to the seed of plants containing at least one heterologous gene which allows the expression of a polypeptide or peptide having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. Preferably, this heterologous gene is from *Bacillus* sp., the gene product having activity against the European corn borer and/or the Western corn rootworm. Particularly preferably, the heterologous gene originates from *Bacillus thuringiensis.*

In the context of the present invention, the active compound combinations or compositions according to the invention are applied on their own or in a suitable formulation to the seed. Preferably, the seed is treated in a stable state, so that the treatment does not cause any damage. In general, treatment of the seed may take place at any point in time between harvesting and sowing. Usually, the seed used is separated from the plant and freed from cobs, shells, stalks, coats, hairs or the flesh of the fruits.

Thus, it is possible to use, for example, seed which has been harvested, cleaned and dried to a moisture content of less than 15% by weight. Alternatively, it is also possible to use seed which, after drying, has been treated, for example, with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

The compositions according to the invention can be applied directly, that is to say without comprising further components and without having been diluted. In general, it is preferable to apply the compositions to the seed in the form of a suitable formulation. Suitable formulations and methods for the treatment of seed are known to the person skilled in the art and are described, for example, in the following documents: U.S. Pat. Nos. 4,272,417, 4,245,432, 4,808,430, 5,876,739, US 2003/0176428 A1, WO 2002/080675 A1, WO 2002/028186 A2.

The good fungicidal activity of the active compound combinations according to the invention is demonstrated by the example below. Whereas the individual active compounds have weaknesses in the fungicidal activity, the combinations exhibit an activity which exceeds a simple addition of activity.

In fungicides, a synergistic effect is always present when the fungicidal activity of the active compound combinations is greater than the expected activity which, for a given combination of 2 or 3 active compounds, is calculated as follows according to S. R. Colby ("Calculating Synergistic and Antagonistic Responses of Herbicide Combinations", Weeds 1967, 15, 20-22):

If

X is the efficacy when active compound A is applied at an application rate of m g/ha, Y is the efficacy when active compound B is applied at an application rate of n g/ha, $E_1$ is the efficacy when the active compounds A and B are applied at application rates of m and n g/ha, respectively, and $E_2$ is the efficacy when the active compounds A and B and C are applied at application rates of m and n and r g/ha, respectively, then $$E_1 = X + Y - \frac{X \cdot Y}{100} \text{ or}$$

$$E_2 = X + Y + Z - \frac{(X \cdot Y + X \cdot Z + Y \cdot Z)}{100} + \frac{X \cdot Y \cdot Z}{10000}$$

Here, the efficacy is determined in %. 0% means an efficacy which corresponds to that of the control, whereas an efficacy of 100% means that no infection is observed.

If the actual fungicidal activity is greater than calculated, the activity of the combination is superadditive, i.e. a synergistic effect is present. In this case, the efficacy actually observed must be greater than the value, calculated using the formula given above, for the expected efficacy $E_1$.

The invention is illustrated by the example below. (However, the invention is not limited to the example.)

EXAMPLE

Rhizoctonia solani Test (In Vitro)/Microtitre Plates

The microtest is carried out in microtitre plates using Potato Dextrose Broth (PDB) as liquid test medium. The active compounds are used as technical-grade a.i., dissolved in methanol. For inoculation, a mycelium suspension of Rhizoctonia solani is used. After 5 days of incubation in the dark and with shaking (10 Hz), the transparency of each filled cavity of the microtitre plates is determined with the aid of a spectrophotometer.

Here, 0% means an efficacy which corresponds to the growth in the controls, whereas an efficacy of 100% means that no fungal growth is observed.

The table below clearly shows that the activity found for the active compound combination according to the invention is greater than the calculated activity, i.e. that a synergistic effect is present.

TABLE

Rhizoctonia solani test (in vitro)/microtest

| Active compound known: | | Application rate of active compound in ppm | % efficacy |
|---|---|---|---|
| N-[2-(1,3-Dimethylbutyl)phenyl]-5-fluoro-1,3-dimethyl-1H-pyrazole-4-carboxamide & metalaxyl | | 0.2 | 64 |
| Tebuconazole | | 0.1 | 13 |

| Mixture according to the invention: | | | | |
|---|---|---|---|---|
| | Mixing ratio | Application rate of active compound in ppm | Actual efficacy | Expected value calculated using Colby's formula |
| N-[2-(1,3-Dimethylbutyl)-phenyl]-5-fluoro-1,3-dimethyl-1H-pyrazole-4-carboxamide & metalaxyl + tebuconazole | 2:1 | 0.2 + 0.1 | 82 | 69 |

Leptosphaeria nodorum Test (Wheat)/Protective

Solvent: 50 parts by weight of N,N-dimethylacetamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the active compound preparation at the stated application rate. After the spray coating has dried on, the plants are sprayed with a spore suspension of Leptosphaeria nodorum. The plants remain in an incubation cabin at 20° C. and 100% relative atmospheric humidity for 48 hours.

The plants are placed in a greenhouse at a temperature of about 20° C. and a relative atmospheric humidity of 80%.

Evaluation is carried out 10 days after the inoculation. Here, 0% means an efficacy which corresponds to that of the control, whereas an efficacy of 100% means that no infection is observed.

TABLE

Leptosphaeria nodorum test (wheat)/protective

| Active compounds | Application rate of active compound in g/ha | Efficacy in % found* | calc.** |
|---|---|---|---|
| (I) N-[2-(1,3-Dimethylbutyl)phenyl]-5-fluoro-1,3-dimethyl-1H-pyrazole-4-carboxamide | 62.5 | 0 | |
| (II) Tebuconazole | 62.5 | 56 | |
| (III) Metalaxyl | 125 | 11 | |
| (I) + (II) 1:1 | 62.5 + 62.5 | 78 | 56 |
| (I) + (III) 1:2 | 62.5 + 125 | 22 | 11 |
| (II) + (IV) 1:2 | 62.5 + 125 | 78 | 60 |
| (I) + (II) + (III) 1:1:2 | 62.5 + 62.5 + 125 | 89 | 60 |

*found = activity found
**calc. = activity calculated using Colby's formula

Pyrenophora teres Test (Barley)/Protective
Solvent: 50 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration, or a commercial formulation of active compound or active compound combination is diluted with water to the desired concentration.

To test for protective activity, young plants are sprayed with the active compound preparation at the stated application rate. After the spray coating has dried on, the plants are sprayed with a conidia suspension of Pyrenophora teres. The plants remain in an incubation cabin at 20° C. and 100% relative atmospheric humidity for 48 hours.

The plants are then placed in a greenhouse at a temperature of about 20° C. and a relative atmospheric humidity of about 80%.

Evaluation is carried out 10 days after the inoculation. Here, 0% means an efficacy which corresponds to that of the control, whereas an efficacy of 100% means that no infection is observed.

TABLE

Pyrenophora teres test (barley)/protective

| Active compound | Application rate of active compound in g/ha | Efficacy in % found* | calc.** |
|---|---|---|---|
| (I) N-[2-(1,3-Dimethylbutyl)phenyl]-5-fluoro-1,3-dimethyl-1H-pyrazole-4-carboxamide | 62.5 | 67 | |
| (II) Prothioconazole | 62.5 | 44 | |
| (III) Metalaxyl | 62.5 | 0 | |
| (I) + (II) 1:1 | 62.5 + 62.5 | 89 | 81 |
| (I) + (III) 1:1 | 62.5 + 62.5 | 78 | 67 |
| (II) + (III) 1:1 | 62.5 + 62.5 | 67 | 44 |
| (I) + (II) + (III) 1:1:1 | 62.5 + 62.5 + 62.5 | 94 | 81 |

*found = activity found
**calc. = activity calculated using Colby's formula

The invention claimed is:

1. An synergistic active compound composition, comprising
    (1) N-[2-(1,3-dimethylbutyl)phenyl]-5-fluoro-1,3-dimethyl-1H-pyrazole-4-carboxamide or salts thereof, and
    (2) at least one acylalanine selected from the group consisting of metalaxyl, metalaxyl-M, and a salt thereof; and
    (3) at least one triazole selected from the group consisting of tebuconazole, prothioconazole, and a salt thereof, wherein 0.1-10 parts by weight of acylalanine (2) and 0.1-10 parts by weight of N-[2-(1,3-dimethylbutyl)phenyl]-5-fluoro-1,3-dimethylyl-1H-pyrazole-4-carboxamide are used per part be weight of triazole (3).

2. A synergistic active compound composition according to claim 1, where the acylalanine (2) is (2-3) metalaxyl.

3. A synergistic active compound composition according to claim 1, where the azole (3) is (3-15) prothiconazole, and/or a salt thereof.

4. A synergistic active compound composition according to claim 1, where the acylalanine (2) is selected from the group consisting of metalaxyl and metalaxyl-M and the triazole (3) is tebuconazole.

5. A composition according to claim 1, further comprising at least one auxiliary, solvent, carrier, surfactant and/or extender.

6. A synergistic active compound composition according to claim 1 capable of controlling unwanted phytopathogenic fungi in crop protection and/or capable of use in the protection of materials.

7. Seed treated with an active compound composition according to claim 1.

8. A synergistic active compound composition according to claim 1, wherein components (1), (2), and (3) are present in a ratio of 1:1:1.

9. A synergistic active compound composition according to claim 1, wherein components (1), (2), and (3) are present in a ratio of 1:2:1.

10. Method for controlling phytopathogenic fungi in crop protection or in the protection of materials, comprising applying a synergistic active compound composition according to claim 1 to a seed, the plant, to fruits of plants and/or to soil on which the plant grows and/or is supposed to grow.

11. A method according to claim 10, wherein in the treatment of leaves from 0.1 to 10 000 g/ha are used, in the treatment of seed from 0.01 to 200 g per 100 kg of seed are used and in the soil treatment from 0.1 to 10 000 g/ha are used.

12. The method of claim 10, wherein the synergistic active compound composition is applied to a seed.

13. The method of claim 10, wherein the synergistic active compound composition is applied to a transgenic plant.

14. The method of claim 10, wherein the synergistic active compound composition is applied to a seed of transgenic plant.

15. A method to control phytopathogenic fungi in crop protection or in the protection of materials by applying simultaneously or in succession an effective amount of:
    (1) N-[2-(1,3-dimethylbutyl)phenyl]-5-fluoro-1,3-dimethyl-1H-pyrazole-4-carboxamide or salts thereof, and
    (2) at least one acylalanine selected from the group consisting of metalaxyl, metalaxyl-M, and a salt thereof; and
    (3) at least one triazole selected from the group consisting of tebuconazole, prothioconazole, and a salt thereof, to the seed, the plant, to fruits of plants and/or to soil on which the plant grows and/or is supposed to grow, wherein 0.1-10 parts by weight of acylalanine (2) and 0.1-10 parts by weight of N-[2-(1,3-dimethylbutyl)phenyl]-5-fluoro-1,3-dimethylyl-1H-pyrazole-4-carboxamide are used per part be weight of triazole (3).

* * * * *